United States Patent
Gelernt (10) Patent No.: US 6,509,194 B1
(45) Date of Patent: Jan. 21, 2003

(54) METHOD AND APPARATUS FOR DETERMINING CONCENTRATION OF NH-CONTAINING SPECIES

(76) Inventor: Barry Gelernt, 1382 Corte Alveo, Oceanside, CA (US) 92057

( * ) Notice: Subject to any disclaimer, the term of this patent is extended or adjusted under 35 U.S.C. 154(b) by 21 days.

(21) Appl. No.: 09/624,118

(22) Filed: Jul. 24, 2000

Related U.S. Application Data (60) Provisional application No. 60/147,017, filed on Aug. 3, 1999.

(51) Int. Cl.[7] .............................................. G01N 33/00
(52) U.S. Cl. ........................ 436/113; 436/106; 422/83; 422/91
(58) Field of Search ................................ 436/106, 113; 422/83, 91

(56) References Cited

U.S. PATENT DOCUMENTS

| | | |
|---|---|---|
| 4,432,939 A | 2/1984 | Watanabe et al. ............. 422/93 |
| 5,739,038 A | 4/1998 | Burrows ..................... 436/113 |

OTHER PUBLICATIONS

Matsuda et al. "Formation and quenching of imidogen (NH) fragments in excited states by high energy electron irradiation of helium–ammonia gas mixture", Appl. Radiat. Isot. (1990), 41(8), 757–61.*

Hikida, T. et al. "Formation of imidogen(c1.Pl.) and (A3.Pl.) in the photolysis of ammonia, hydrazoic acid, and isocyanic acid a 121.6 nm", Chem. Phys. (1988), 121(1), 63–71.*

Kenner, R. D. et al. "Two–photon formation of imidogen (NH/ND)(A3.Pl.) in the 193 nm photolysis of ammonia. I. Mechanism and identification of the intermediate species", Chem. Phys. (1987), 118(1), 141–52.*

Hochard, L. et al. "Imidogen (NH) production in an argon + ammonia glow discharge" Symp. Proc.—Int. Symp. Plasma Chem., 6th (1983), vol. 2, 473–7.*

Chowdhury et al. "Isocyanic acid as a laser fuel", Proc. SPIE–Int. Soc. Opt. Eng. (1988), 875 (Short Ultrashort Wavelength Lasers), 173–82.*

Qi et al. ": Direct production of excited fluoroimidogen (NF)(b1.SIGMA.+) in the atomic fluorine –molecular florine—ammonia system via a supersonic regime", Conf. Ser.—Int. Phys. (1985), 72(Gas Flow Chem. Lasers, 1984), 149–52.*

Hack et al. "Reaction of imidogen (X3.SIGMA.–) with dioxygen(3.SIGMA.g–) and dioxygen(1.DELTA.g) in the gas phase", J. Chem. Soc., Faraday Trans. 2 (1985), 81(6), 949–61.*

Hack et al. "Production of electronically excited fluoroimidogen radicals in the system NH3–F–O2 (1Dg)", Chem. Phys. Lett. (1981), 82(2), 327–30.*

Bower et al. "Qenching of NH (a 1D)", J. Chem. Phys., 1987 v. 86 (4), pp. 1954–1956.*

Hack "NH RAdical Reactions", N–Cent. Radicals (1998), 413–466, Ed. Alfassi et al.*

Durie, "The Spectra of Flames Supported by Fluorine", Proceedings of the Royal Society of London, Series A, vol. 211, Mar. 20, 1952, pp. 110–121.

Gaydon, "The Spectroscopy of Flames", Flames with Nitrogen, Halogens, etc., pp. 219–220, 1957.

* cited by examiner

Primary Examiner—Jill Warden
Assistant Examiner—Yelena Gakh
(74) Attorney, Agent, or Firm—Wan-Yee Cheung; Patricia A. Verlangieri; Moser, Patterson & Sheridan, LLP

(57) ABSTRACT

A method and apparatus for determining ammoniacal species concentration in a gas sample. In one embodiment, trace concentration of ammonia in an air sample is determined by monitoring emission intensity from an excited radical species (NH*), which is produced in a reaction between ammonia and fluorine. The observed emission intensity is compared with calibration data obtained from previously analyzed gas samples containing ammonia. The method and apparatus can also be adapted to detect ammoniacal species concentration in other NH-containing gas samples.

13 Claims, 2 Drawing Sheets

METHOD AND APPARATUS FOR DETERMINING CONCENTRATION OF NH-CONTAINING SPECIES

CROSS REFERENCES AND RELATED APPLICATION

This application claims priority to U.S. provisional patent application Ser. No. 60/147,017, entitled "Method and Apparatus for Determining Concentration of NH-Containing Species," filed on Aug. 3, 1999, which is herein incorporated by reference.

BACKGROUND OF THE DISCLOSURE

1. Field of the Invention

The invention relates generally to a method and apparatus of determining gas phase species concentration, and more particularly, to a method and apparatus for detecting concentration of NH-containing species.

2. Description of the Background Art

The use of ammonia ($NH_3$), a corrosive and toxic gas, in industrial processes is wide spread. Trace amount of $NH_3$ has also been shown to adversely impact the use of chemically activated deep ultraviolet photoresists in advanced semiconductor fabrication. The need for worker protection, from either acute exposure to high $NH_3$ concentrations or long term exposure to very low concentration levels, has resulted in the development of sampling methods for the detection and quantitative measurement of $NH_3$ in ambient air. Some existing analytical techniques for $NH_3$ detection are briefly described below.

a. Electrochemical Method

In this method, gaseous $NH_3$ is absorbed into an electrochemical sensor assembly with a resultant change in the electrical conductivity of the sensor cell. The increased current flow allowed by the sensor is fairly linear over the concentration range of 1–50 ppm. A lower detection limit is about 500 ppb, but reproducibility of the sensor to periodic exposure of $NH_3$ is only fair.

b. Ozone Method

This method uses a reaction between ozone ($O_3$) and ammonia, in which $NH_3$ is first converted to $NO_2$, followed by a chemiluminescent reaction between $NO_2$ and $O_3$. The reaction with $O_3$ results in the formation of excited state $NO_2$ molecules, denoted as $NO_2^*$, and the intensity of emission from $NO_2^*$ is used to determine the original $NH_3$ concentration. However, difficulties in quantitative measurement result from side reactions during the conversion from $NH_3$ to oxides of nitrogen (forming NO and, perhaps, $NO_3$ or HNO), and also from non-stoichiometric side reactions between $NO_2$ and $O_3$. In addition, the emission from excited $NO_2$ species ($NO_2^*$—the asterisk "*" is used in this disclosure to designate an excited state of a species) extends from the near UV into the yellow-green region of the visible spectrum (this emission is the well known "air afterglow" in the night sky, and results from the reaction: $NO+O_2 \rightarrow NO_2^*+O$). Detection of this very diffuse emission over a broad spectral region is susceptible to interference from other emitting species, and may pose difficulties in accurate concentration determination.

c. Air Sampling Method

In this method, air samples are collected via a carefully prepared evacuated sampling ampoule and injected into a gas chromatograph (GC) for comparison against analyzed standards by well known methods. Careful selection of the GC column and temperature settings are necessary in order to obtain reliable results. A number of detectors are available for this method. One very sensitive detection method is mass spectrometry, but calibration for quantitative work is very difficult. Additionally, the GC/MS method is very expensive, and it is difficult to configure in a continuous sampling mode.

d. Laser Induced Emission

This method has the potential for great sensitivity, but requires great expertise and expense due to its sophistication. $NH_3$, or a fragment thereof, is electronically (or vibrationally) excited by a pulsed, tunable dye laser, thereby creating observable fluorescence. However, non-linear optical effects and saturation effects tend to make quantitative measurements extremely complex, if at all possible.

Each of these prior art techniques has its own limitation and varying degrees of experimental complexities. Therefore, a need exists in the art for alternative analytical methods which allow continuous on-line determination of low level of ammonia in ambient air or gas samples.

SUMMARY OF THE INVENTION

Embodiments of the invention generally provides a method and apparatus for determining the concentration of an NH-containing species in a gas sample. The method comprises detecting radiation from excited imidogen radicals (NH*) generated from the gas sample, and determining the concentration of the NH-containing species from calibration data correlating detected NH* radiation intensity with concentration of the NH-containing species. In one embodiment, the NH-containing species is ammonia ($NH_3$), and the NH* radiation is generated by reacting $NH_3$ with a gas sample containing fluorine. Using a bandpass optical device, NH* radiation around 336 nm can be selectively transmitted and detected, with minimal interference from other emitting species.

BRIEF DESCRIPTION OF THE DRAWINGS

The teachings of the present invention can readily be understood by considering the following detailed description in conjunction with the accompanying drawings, in which.

To facilitate understanding, identical reference numerals have been used, where possible, to designate identical elements that are common to the figures.

DETAILED DESCRIPTION

The present invention generally provides a method and apparatus for determining concentration of an ammoniacal (ammonia-like, or NH-containing) species in a gas sample. In one embodiment, the ammoniacal species is ammonia ($NH_3$). It is known to those skilled in the art of molecular spectroscopy that gaseous $NH_3$ and molecular fluorine ($F_2$) will spontaneously react, typically at sub-atmospheric pressures. As is the case with many gas phase reactions, several chemical reaction pathways are possible, giving rise to different reactive or non-reactive intermediate or product species. It is also known that light emission accompanies this spontaneous reaction, and that the emission is characteristic of energetic, or excited state, species generated in the reaction. Among these electronically excited species is the diatomic imidogen free radical (NH*), which has a spectral emission in an unusually narrow wavelength region around 336 nm (due to the NH $A^3\Pi$-$X^3\Sigma^-$ transition). This light emission, also known as fluorescence, is the predominant emission in the visible and ultra-violet (UV) region of the optical spectrum from the spontaneous reaction between $NH_3$ and $F_2$. When the emission is generated from a chemical reaction, it is sometimes referred generally as chemiluminescence.

Embodiments of the invention provides a method and apparatus by which a trace concentration of $NH_3$ can be determined from a functional relationship between the $NH_3$ concentration and the observed NH* emission intensity, where NH* is used to denote generally an excited state of the NH species. In particular, the method relies on two assumptions: 1) that the detected NH* emission intensity ($I_{NH}*$) is proportional to the concentration of NH* species; and 2) that the concentration of NH* is in turn correlated with the initial $NH_3$ concentration prior to the reaction with $F_2$.

The first assumption can be expressed as:

$$I_{NH}* = k*[NH*] \qquad \text{Eq.(1)};$$

where k* is a proportionality constant related to a variety of factors specific to the experimental setup, including light collection efficiency, detector sensitivity, and the like; and [NH*] is the concentration of excited NH species present in the detection volume.

The second assumption can be expressed as:

$$[NH*] = k_1 f([NH_3]) \qquad \text{Eq.(2)};$$

where $k_1$ is a proportionality constant, and $f([NH_3]$ denotes generally a function of the concentration of $NH_3$. Again, $k_1$ is an experimental constant which depends on a variety of factors related to the reaction kinetics between $NH_3$ and $F_2$. This, along with Eq. (1) above, leads to:

$$I_{NH}* = kf([NH_3]) \qquad \text{Eq.(3)};$$

where $k = k*k_1$.

According to the method of the invention, the concentration of $NH_3$ present in a gaseous sample can be determined by experimentally measuring the intensity of emission from NH*, and determining the $NH_3$ concentration $[NH_3]$ from the functional relationship of Eq. (3). The exact functional relationship $f([NH_3])$ can be obtained by a calibration procedure to be described below. The method is particularly suited to the determination of trace level of $NH_3$ in a gas sample.

In general, the concentration of an intermediate species in a reaction, such as an excited state of a reactive radical (NH*), is very low, and one may encounter difficulties in detecting emission from such a species. However, one can take advantage of the fact that the predominant visible and UV emission from the $NH_3+F_2$ reaction originates from NH*. By using a suitable bandpass optical device, such as an optical interference filter or monochromator, one can selectively transmit and detect the NH* emission around 336 nm to the exclusion of background signal from other emitting species. Any background emission, if not properly excluded, may interfere with (i.e., contribute to) the observed light emission intensity and thus affect the accuracy of the determination of $NH_3$ concentration.

Since the reaction between $NH_3$ and $F_2$ occurs in the absence of heating or other external energy sources (i.e., as a "dark reaction"), the resulting fluorescence can be measured against a dark background. This allows the use of extremely sensitive light detection methods, such as photon-counting, to detect and quantify trace amounts of $NH_3$ present in a gas sample, such as an ambient air sample containing $NH_3$. Hence, the invention has superior sensitivity over existing methods.

Figure 1:
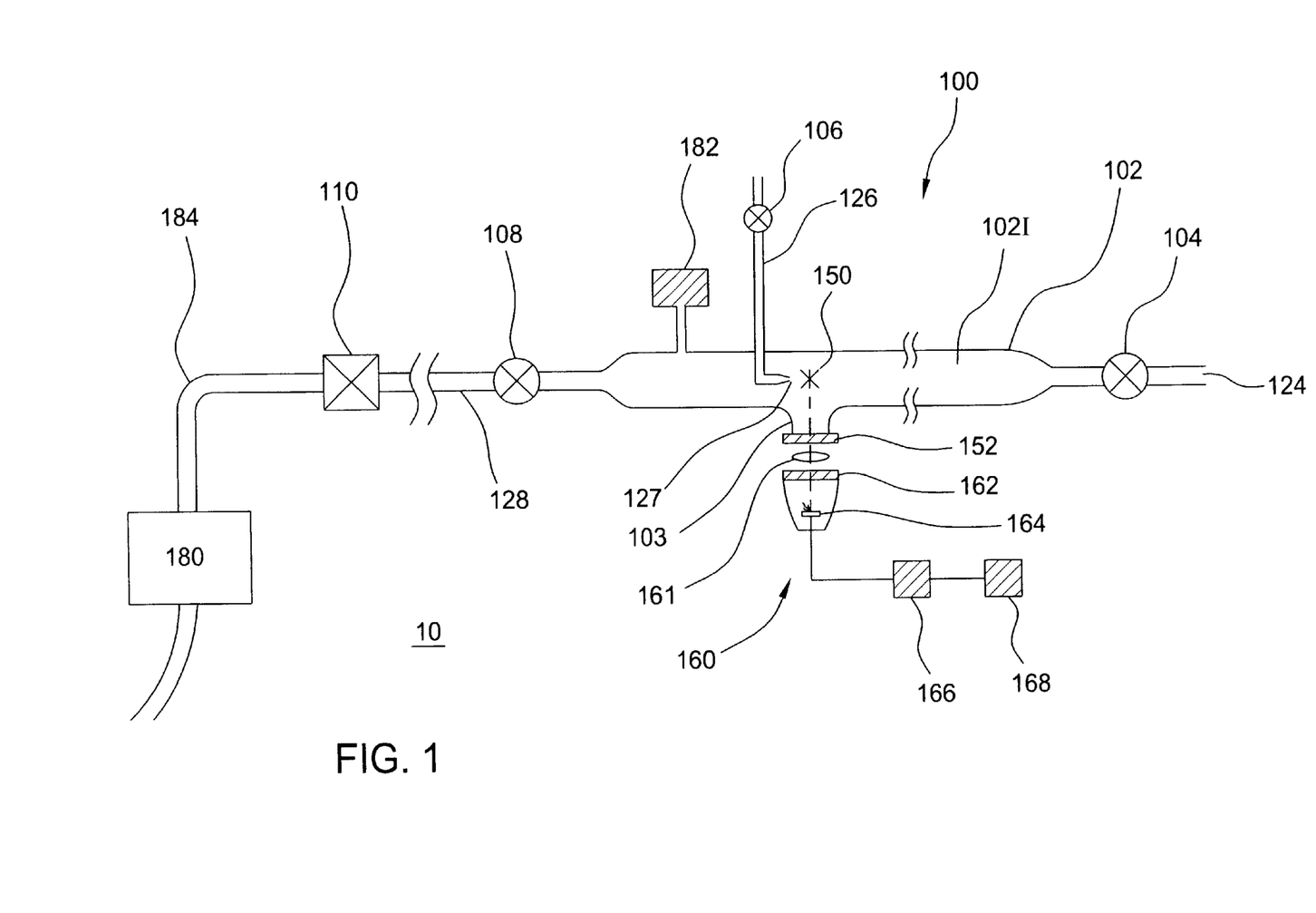
FIG. 1 depicts a schematic diagram of an apparatus for determining ammonia concentration according to one embodiment of the invention.

An apparatus suitable for practicing the present invention is illustrated schematically in FIG. 1. The apparatus 10 comprises a vacuum system 100 and an optical detection system 160. The vacuum system 100 further comprises a reaction vessel 102 (or reactor) connected to a pressure-reducing device such as a vacuum pump 180 and other gas flow and pressure regulating components. As shown in FIG. 1, the gas flow and pressure regulating components may illustratively comprise vacuum valves 104, 106, 108 and 110. The valve 104 controls gas flow at the inlet 124, while the valve 108 controls gas flow at the outlet 128. At least one of these valves 104, 108 should have an adjustable orifice for variable gas flow control, such as that provided by a needle valve. Different needle valves with varying sizes of orifices can result in a fine control of the gas flow up to a range of, for example, 500 sccm. The exact flow range, however, is not critical to the practice of the present invention.

The valve 110 is a throttle valve connecting the outlet 128 to the vacuum pump 180 via a vacuum line 184. For example, the vacuum pump 180 may be a mechanical pump with inert fluorocarbon oil having a 2 CFM pumping capacity. The exhaust gases, including carrier gas, reactant and product gases, are evacuated through the vacuum line 184. The pumping capacity (or speed) provided to the vessel 102 can be varied by adjusting the throttle valve 110. The adjustment of valves 104 and 108, in conjunction with the throttle valve 110, allows control of the gas flows through the vessel 102. Thus, a partial vacuum in the range of about 0.1 mbar to about 50 mbar can be achieved inside the vessel 102. A pressure transducer 182 is also provided for pressure measurement. It is preferable that more than one pressure gauge be used for pressure monitoring at different pressure ranges. For example, capacitance manometers available from MKS Instruments, Inc., Andover, Ma., are suitable for this purpose.

The reaction vessel 102 also comprises a second inlet 126. A valve 106 is used to control the gas flow through the inlet 126, which extends into the interior 102I of the vessel 102, and terminates in an inlet tip 127. An optical window 152 is provided on one side 103 of the vessel 102 at close proximity to the inlet tip 127. The reaction vessel 102 is preferably made of glass or quartz, but other materials such as stainless steel are also acceptable, as long as it is compatible with the chemicals or gases used. The optical window 152 should be made of a material which can transmit radiation around 336 nm. In general, any ultra-violet (UV) transmitting materials such as different grades of quartz will suffice.

To perform the $NH_3$ concentration measurement according to embodiments of the invention, the vessel 102 is evacuated with the throttle valve 110 and valve 108 fully open. After a base pressure of about 0.1 mbar or below is reached, the valve 108 is closed to some appropriate intermediate position while a gas sample to be analyzed, e.g., air containing an unknown concentration of $NH_3$, is introduced into the vessel 102 via the inlet 124. The flow rate of this $NH_3$/air sample through the vessel 102 can be controlled by adjusting the valves 104 and 108. A steady flow of the gas sample may be established within a range of about 100–500 sccm, preferably at about 300 sccm. An operating pressure in the range of about 0.1 mbar to about 50 mbar, preferably at about 10 mbar, may be used.

With the $NH_3$/air flow rate and pressure established, a second gas sample containing fluorine—e.g., a dilute mixture of $F_2$ in a carrier gas such as argon (Ar) or helium (He), is then is introduced into the vessel 102 through the inlet 126 by the valve 106. This fluorine-containing gas sample, also referred to as a reactant gas, is used to initiate a reaction between $NH_3$ and $F_2$. The reactant gas is preferably a highly diluted mixture of $F_2$ in a non-reactive carrier gas such as ultra-high purity (UHP) Ar or UHP He. Of course, other similarly non-reactive or inert gases, e.g., nitrogen ($N_2$), may also be used as a carrier gas, provided that they do not substantially interfere either with the $NH_3+F_2$ reaction or the detection of the NH* emission. The $F_2$/carrier gas mixes with and reacts with the flow of air containing $NH_3$ (or generally, the gas sample to be analyzed) just down-stream of the gas inlet tip 127. This counter-flow reaction method and apparatus design is well known in experimental gas kinetics.

A reaction zone 150, where $F_2$ and $NH_3$ reaction occurs, is generally defined in the vicinity of the reactant gas inlet tip 127 inside the vessel 102. By controlling the flow rate of the $F_2$ gas into the air/$NH_3$ flow stream, one can confine the reaction zone 150 to within a relatively small, well-defined volume. A better defined reaction zone 150 is preferable because it allows an efficient collection and detection of the chemiluminescence.

As the reactant gas reacts with $NH_3$ in the $NH_3$/air sample, emission from excited NH* species is detected using the optical detection system 160 to be described below. The reactant gas flow should be adjusted so as to maximize the NH* emission intensity $I_{NH}$* detected by the optical detection system 160. That is, at a fixed flow rate of $NH_3$/air, the reactant gas flow should be sufficiently high such that additional $F_2$ (or reactant gas) will not result in an increase of detected $I_{NH}$* signal for a given configuration of the optical detection system 160.

It is understood that the process parameters disclosed herein are meant to be illustrative, and other gas flow rates and operating pressures may be adjusted as appropriate to different reaction vessels. In general, the choice of the operating pressure may be based on several considerations—e.g., a higher operating pressure tends to favor a higher reaction rate between $NH_3$ and $F_2$. However, a higher pressure also results in increased collisions between the excited NH* and other gas molecules. These collisions may lead to "quenching" of the NH* emission, and thereby reduce the amount of detectable optical signal. Therefore, an optimal operating pressure may involve balancing these competing considerations, and one can experimentally arrive at the desired operating pressure by establishing initial flows of the $NH_3$ and $F_2$ gases, and adjusting valves 104, 106, and 108 to maximize the NH* signal. Such optimization technique is well-known to one skilled in the art of chemical kinetics.

If the gas sample to be analyzed is being used as a process gas in a certain process application, the apparatus 10 may also be used for continuous on-line measurement of $NH_3$ concentration in the process gas. For example, the apparatus 10 may be connected (e.g., at its inlet 124) to a reactor (not shown) used for the particular process application, and a relatively small flow of the process gas may be diverted from the reactor into the reaction vessel 102 via the inlet 124. The $NH_3$ concentration may then be continuously monitored according to embodiments of the invention, without interfering with the particular process application.

Optical Detection System

The light emission from the reaction of $NH^3$ and $F_2$ (due to the NH $A^3\Pi$-$X^3\Sigma^-$ transition), is transmitted through a suitable optical window 152 and a bandpass optical device 162, and detected by a detector 164. A lens 161, or similar imaging optics, may also be used to facilitate the collection and imaging of light emission from a sample volume (e.g., the reaction zone 150) onto the detector 164.

The bandpass optical device 162 preferably has a bandpass that is sufficiently narrow as to transmit the NH* emission near 336 nm, while substantially rejecting emissions from other species that may interfere with the detection of the NH* emission (i.e., selectively transmitting the desired NH* emission). In one embodiment of the invention, a narrow bandpass filter 162, e.g., an interference filter having a bandpass of about 10 nm (i.e., full-width bandpass at half-maximum intensity, or FWHM), with a peak transmission of about 10–50% around 336 nm may be used. Due to the "piling-up" of the Q-branch of the NH $A^3\Pi$-$X^3\Sigma^-$ electronic transition, most of the NH* chemiluminescence can be transmitted through the interference filter 162, which also effectively blocks other undesirable or background emissions, thus facilitating the detection of NH* emission. Such an interference filter is available from commercial optics supply vendors. The optical characteristics of the interference filter cited herein are meant to be illustrative. It is understood that filters with different optical characteristics (i.e., FWHM bandpass, peak transmission percent and peak wavelength) may also be used to transmit the NH* emission for practicing embodiments of the invention. For example, if measures are taken to eliminate interfering emissions (e.g., by eliminating species having interfering emissions), a wider bandpass filter may be tolerated.

In other embodiments, the bandpass optical device 162 may comprise a combination of different filters that is effective for selectively transmitting the desired NH* emission, while blocking interfering emissions from other species. For example, the combination may include a longpass filter and a shortpass filter with appropriate cut-off wavelengths, or a bandpass filter having a FWHM bandpass larger than about 10 nm and a suitable cut-off filter. One example of a possible interfering emission originates from OH radicals, which may arise from the presence of moisture or other reactions in the reactor. It is known that an excited state of the OH radical has a strong emission around 306 nm. If a short wavelength cut-off filter (or longpass filter) is used to block the 306 emission from excited OH radicals, then a filter having a FWHM bandpass larger than about 10 nm may be used. Other bandpass optical devices such as a monochromator or similar equipment with wavelength selection capabilities can also be used in place of an interference filter.

The light emission that passes through the bandpass device or filter 162 is incident upon the detector 164, which is selected to be sensitive to the transmitted emission. For example, the detector 164 may be a RCA 1P28 photomultiplier tube operating at about 800V DC. The photocurrent generated by the emission can be detected using commercially available detection and amplification equipment 166. Suitable detection and amplification equipment 166 may include picoammeters or photon-counting devices with dynode pulse discrimination electronics, among others. In general, various combinations of detectors and amplification equipment may be used to detect the emission through the optical device 162 and convert it to a radiation intensity parameter that correlates with the intensity of the NH* emission. The apparatus 10 should preferably include a device 168 for monitoring and/or recording of the amplified optical signal, or more generally, the radiation intensity parameter. The device 168 may illustratively be a computer which interfaces with the detection and amplification equipment 166 and provides for data storage and retrieval.

Calibration of the apparatus 10 is accomplished with dilute, analyzed samples containing $NH_3$—e.g., $NH_3$ in $N_2$ or in air, or other suitable carrier gases. A calibration plot, for example, is constructed by plotting the chemiluminescent intensity during reaction with excess $F_2$ against known $NH_3$ concentrations [$NH_3$] from analyzed, calibration gas samples.

Calibration Procedure

In order to determine the concentration of $NH_3$ in an unknown gas sample, a calibration procedure is performed in the reaction vessel 102 to generate calibration data which correlate detected NH* emission intensities with known $NH_3$ concentrations in calibration gas samples. The calibration gas samples, e.g., $NH_3$/air mixtures, can be analyzed to obtain known $NH_3$ concentrations by conventional analytical methods, or prepared by successive dilutions from more concentrated mixtures that are amenable to conventional analytical techniques, or procured as analyzed mixtures from any number of industrial gas suppliers.

The calibration procedure involves experimentally measuring the NH* emission intensities ($I_{NH}^*$) from reaction with $F_2$ for several calibration gas samples with known $NH_3$ concentrations [$NH_3$], using the procedure previously described. For example, NH* emission measurements can be performed for each of several calibration gas samples containing $NH_3$ concentrations between a few hundred to a few thousand parts per billion (ppb) by mixing each of the calibration gas samples with a reactant gas containing fluorine. Although the fluorine-containing reactant gas used in the calibration procedure may be different from that used in the reaction with the gas sample having the unknown $NH_3$ concentration, it is preferable and more convenient to use the same reactant gas (e.g., similar $F_2$ concentration and/or carrier gas).

Figure 2:
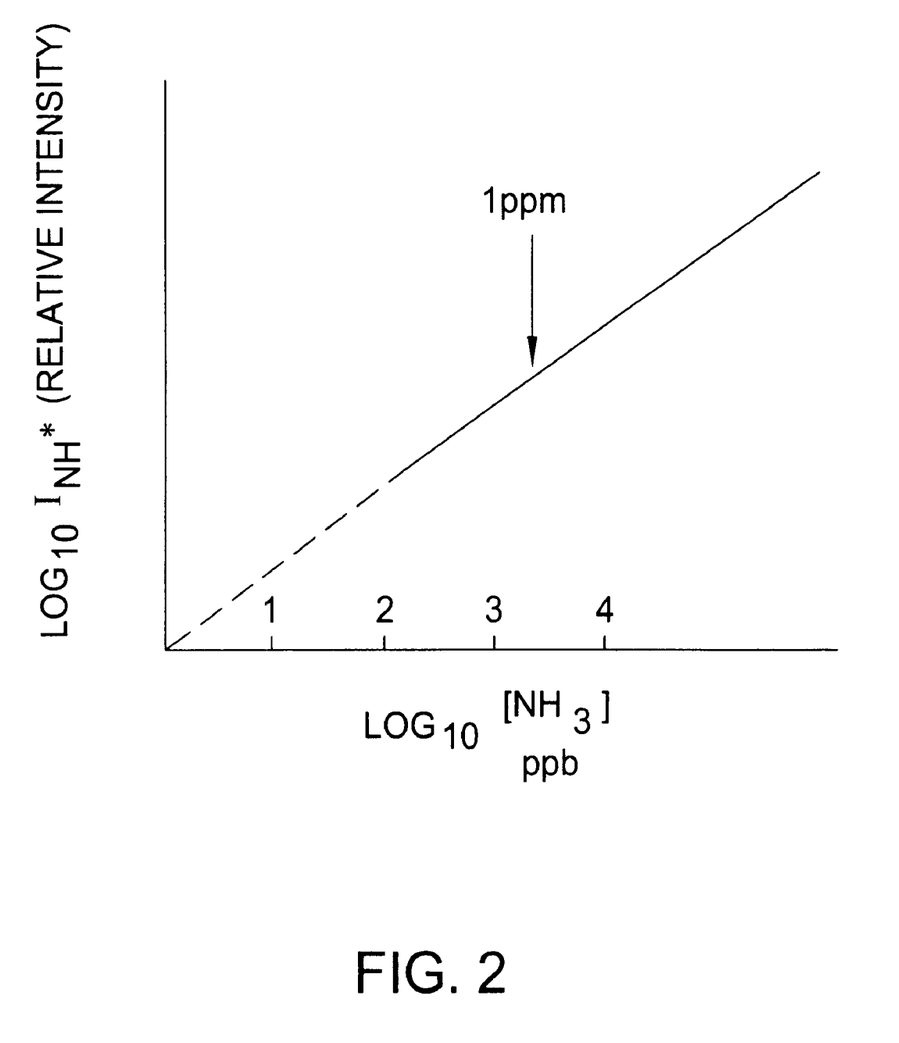
FIG. 2 is an illustration of a calibration plot which can be used for determining concentration of ammoniacal species.

The calibration data comprising detected emission intensity $I_{NH}^*$ (or a calibrated radiation intensity parameter correlating with $I_{NH}^*$) and its corresponding $NH_3$ concentration [$NH_3$] may be represented in a calibration plot, such as that illustrated in FIG. 2, which can be extrapolated to lower concentrations. More generally, a functional relationship between $I_{NH}^*$ and [$NH_3$] can be derived from the calibration data. The $NH_3$ concentration in a gas sample with an unknown [$NH_3$] can then be determined by comparing the observed NH* emission intensity (from a reaction between the $NH_3$-containing gas sample and the reactant gas containing fluorine) with the calibration data, or from the functional relationship correlating NH* emission intensity $I_{NH}^*$ with $NH_3$ concentration.

In one illustrative embodiment, a mixture of 0.5% $F_2$ in UHP Ar can be used as a reactant gas for calibration. In practice, it is not possible to maintain a stable concentration of highly diluted $F_2$ gas in a vessel (gas cylinder) for an extended period of time due to the corrosive or reactive nature of $F_2$. However, this will not affect the calibration procedure because $F_2$ is introduced in "excess" to produce a maximum detected $I_{NH}^*$ for the given detection system 160. The reaction vessel 102 is first evacuated to a pressure of about 0.1 mbar. After a steady flow of one calibration $NH_3$/air sample (i.e., previously analyzed, with known $NH_3$ concentration) is established, e.g., at a pressure of about 10 mbar and a flow rate of about 300 sccm (or generally, the same pressure and flow rate as used for the reaction with the gas sample having unknown $NH_3$ concentration), the $F_2$/Ar reactant mixture is introduced into the vessel 102 at the inlet tip 127. To ensure that $F_2$ is in "excess", the $F_2$/Ar reactant gas is introduced until the observed NH* emission intensity no longer increases with additional $F_2$/Ar reactant mixture. The NH* emission from the reaction zone 150 is detected as described above using detector 164.

The observed intensity $I_{NH}^*$, along with the known concentration of the previously analyzed $NH_3$/air sample, may be recorded or stored in a suitable medium, e.g., a computer. The calibration procedure is repeated for the remainder of the calibration gas samples (that have previously been analyzed to obtain known $NH_3$ concentrations). A calibration plot such as that shown in FIG. 2 can be recorded, showing the observed intensity $I_{NH}^*$ vs. the known $NH_3$ concentration. In general, a functional relationship derived from the calibration data will be used for the determination of $NH_3$ concentration in gas samples. The calibration results should ideally be recorded by electronic means, for example, a computer or processor having a storage device, to facilitate data storage and retrieval.

Other NH-Containing Samples

Although the present embodiment focuses on the measurement of $NH_3$ in a gas sample, this invention can be extended to the determination of other ammoniacal, or ammonia-like species, e.g., molecular species with a N—H bond, such as organic amines, imines and other NH-containing species. Although the detailed chemical reactions may differ, it is anticipated that reactions between different ammoniacal species and fluorine (contained in the reactant gas sample) will lead to the formation of excited NH species, or NH*. Depending on the specific ammoniacal species, the reaction may not be "dark", as previously explained for the case of $NH_3$. However, the use of a narrowband interference filter should still suffice to isolate the emitted radiation from NH*, for example, around 336 nm, to allow for a determination of the ammoniacal species concentration. Of course, a separate calibration procedure has to be performed as previously described for a number of the gas samples containing known concentrations of the species of interest. The choice of pressure and flow parameters used in the $F_2$ reaction can readily be arrived at through experimentation which is known to those skilled in the art of chemical kinetics.

Although one embodiment which incorporate the teachings of the present invention has been shown and described in detail herein, those skilled in the art can readily devise many other varied embodiments that still incorporate these teachings.

What is claimed is:

1. A method for determining ammonia ($NH_3$) concentration, comprising the steps of:
   (a) providing at least one of calibration data regarding ammoniacal species concentration or a functional relationship correlating detected radiation from excited imidogen radicals with ammoniacal species concentration;
   (b) mixing a first gas sample containing ammonia ($NH_3$) with a second gas sample containing fluorine;
   (c) detecting radiation from excited imidogen radicals generated from said step (b); and
   (d) determining ammonia ($NH_3$) concentration in said first gas sample based on a comparison of the radiation detected in said step (c) with said at least one of calibration data regarding ammoniacal species concentration or said functional relationship correlating detected radiation from excited imidogen radicals with ammoniacal species concentration provided in said step (a).

2. The method of claim 1, wherein said step (c) further comprises the steps of:
   (c1) providing an optical device to selectively transmit radiation at a wavelength around 336 nm;
   (c2) detecting said radiation transmitted through said optical device; and
   (c3) converting said detected radiation Into a radiation intensity parameter.

3. The method of claim 2, wherein said step (a) further comprises the steps of:
   (a1) providing a plurality of calibration gas samples containing ammonia ($NH_3$), each having a different, but known, concentration of ammonia ($NH_3$);
   (a2) mixing one of said plurality of calibration gas samples containing ammonia ($NH_3$) with a reactant gas containing fluorine;
   (a3) detecting radiation emitted from NH* generated from said step (a2);
   (a4) converting said detected radiation from said step (a3) into a calibrated radiation intensity parameter;
   (a5) storing in a storage device said calibration radiation intensity parameter and corresponding known ammonia ($NH_3$) concentration of said one of said plurality of calibration gas samples of the first type; and
   (a6) repeating said steps (a2), (a3), (a4) and (a5) for all of said plurality of calibration gas samples of the first type.

4. The method of claim 3, wherein said step (d) further comprises the step of:
   (d1) comparing said radiation intensity parameter from said step
   (c3) with said at least one of calibration data regarding ammoniacal species concentration or said functional relationship correlating detected radiation from excited imidogen radicals with ammoniacal species concentration from said step (a).

5. A method for determining concentration of an ammoniacal species in a first gas sample comprising the steps of:
   (a) providing at least one of calibration data regarding ammoniacal species concentration or a functional relationship correlating detected radiation from excited imidogen radicals with ammoniacal species concentration;
   (b) detecting radiation from excited imidogen radicals generated from said ammoniacal species in a first gas sample without application of energy from an external energy source; and
   (c) determining concentration of said ammoniacal species in said first gas sample based on a comparison of the radiation detected in said step (b) with said at least one of calibration data regarding ammoniacal species concentration or said functional relationship correlating detected radiation from excited imidogen radicals with ammoniacal species concentration provided in said step (a).

6. The method of claim 5, wherein said excited imidogen radicals in said step (b) are generated by mixing a second gas sample containing fluorine with said first gas sample.

7. The method of claim 5, wherein said step (b) further comprises the steps of:
   (b1) providing an optical device to selectively transmit radiation at a wavelength around 336 nm; and
   (b2) detecting said radiation transmitted through said optical device.

8. The method of claim 5, wherein said step (a) further comprises the steps of:
   (a1) providing a plurality of calibration gas samples of a first type, each having a different, but known, concentration of an ammoniacal species;
   (a2) mixing one of said plurality of said calibration gas samples of the first type with a calibration gas sample of a second type comprising fluorine;
   (a3) detecting radiation emitted from NH* generated from said step (a2);
   (a4) converting said detected radiation from said step (a3) into a calibrated radiation intensity parameter;
   (a5) storing in a storage device said calibrated radiation intensity parameter and corresponding known concentration of said ammoniacal species for said one of said calibration gas samples of the first type; and
   (a6) repeating said steps (a2), (a3), (a4) and (a5) for all of said plurality of calibration gas samples of the first type.

9. The method of claim 8, wherein said step (c) further comprises the steps of:
   (c1) converting said detected radiation from excited imidogen radicals generated from said ammoniacal species in said first gas sample into a radiation intensity parameter, and
   (c2) comparing said radiation Intensity parameter from said step (c1) with said at least one of calibration data regarding ammoniacal species concentration or said functional relationship correlating detected radiation from excited imidogen radicals with ammoniacal species concentration from said step (a).

10. A method for determining ammonia ($NH_3$) concentration, comprising the steps of:
    (a) providing at least one of calibration data regarding ammonia ($NH_3$) concentration or a functional relationship correlating detected radiation from excited imidogen radicals with ammonia ($NH_3$) concentration;
    (b) mixing a first gas sample containing ammonia ($NH_3$) with a second gas sample containing fluorine;
    (c) detecting radiation from excited imidogen radicals generated from said step (b) without application of energy from an external energy source; and
    (d) determining ammonia ($NH_3$) concentration in said first gas sample based on a comparison of the radiation detected in said step (c) with said at least one of calibration data regarding ammonia ($NH_3$) concentration or said functional relationship correlating detected radiation from excited imidogen radicals with ammonia ($NH_3$) concentration provided in said step (a).

11. The method of claim 10, wherein said step (c) further comprises the steps of:
    (c1) providing an optical device to selectively transmit radiation at a wavelength around 336 nm;
    (c2) detecting said radiation transmitted through said optical device; and
    (c3) converting said detected radiation into a radiation intensity parameter.

12. The method of claim 11, wherein said step (a) further comprises the steps of:
    (a1) providing a plurality of calibration gas samples containing ammonia ($NH_3$), each having a different, but known, concentration of ammonia ($NH_3$);
    (a2) mixing one of said plurality of calibration gas samples containing ammonia ($NH_3$) with a reactant gas containing fluorine;
    (a3) detecting radiation emitted from NH* generated from said step (a2);

(a4) converting said detected radiation from said step (a3) into a calibrated radiation intensity parameter;
(a5) storing in a storage device said calibration radiation intensity parameter and corresponding known ammonia ($NH_3$) concentration of said one of said plurality of calibration gas samples of the first type; and
(a6) repeating said steps (a2), (a3), (a4) and (a5) for all of said plurality of calibration gas samples of the first type.

13. The method of claim 12, wherein said step (d) further comprises the step of:
(d1) comparing said radiation intensity parameter from said step (c3) with said at least one of calibration data regarding ammonia ($NH_3$) concentration or said functional relationship correlating detected radiation from excited imidogen radicals with ammonia ($NH_3$) concentration from said step (a).

* * * * *

UNITED STATES PATENT AND TRADEMARK OFFICE
CERTIFICATE OF CORRECTION

PATENT NO. : 6,509,194 B1
DATED : January 21, 2002
INVENTOR(S) : Barry Gelernt

It is certified that error appears in the above-identified patent and that said Letters Patent is hereby corrected as shown below:

<u>Column 8,</u>
Lines 53 and 63, after "at least one" insert -- set --.

<u>Column 9,</u>
Line 11, please change "Into" to -- into --.
Lines 43 and 53, after "at least one" insert -- set --.

<u>Column 10,</u>
Line 26, please change "Intensity" to -- intensity --
Lines 34 and 45, after "at least one" insert -- set --.

Signed and Sealed this

Eighteenth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,509,194 B1
DATED : January 21, 2003
INVENTOR(S) : Barry Gelernt

It is certified that error appears in the above-identified patent and that said Letters Patent is hereby corrected as shown below:

<u>Column 8,</u>
Lines 53 and 63, after "at least one" insert -- set --.

<u>Column 9,</u>
Line 11, please change "Into" to -- into --.
Lines 43 and 53, after "at least one" insert -- set --.

<u>Column 10,</u>
Line 26, please change "Intensity" to -- intensity --.
Lines 34 and 45, after "at least one" insert -- set --.

This certificate supersedes Certificate of Correction issued March 18, 2003.

Signed and Sealed this

Fourteenth Day of October, 2003

JAMES E. ROGAN
*Director of the United States Patent and Trademark Office*